US005800818A

United States Patent [19]

Prugnaud et al.

[11] Patent Number: 5,800,818

[45] Date of Patent: Sep. 1, 1998

[54] MIXTURE COMPRISING PLANT EXTRACTS FOR MOISTURIZING THE UPPER LAYERS OF THE EPIDERMIS

[75] Inventors: Laurent Prugnaud, Vincennes; Christian Lubrano, L'Hayes Les Roses; Anne-Marie Scott De Martinville, Nesle, all of France

[73] Assignee: Laboratoires de Biologie Vegetale Yves Rocher, La Gacilly, France

[21] Appl. No.: 764,752

[22] Filed: Dec. 12, 1996

[30] Foreign Application Priority Data

Dec. 12, 1995 [FR] France ........ 95 14710

[51] Int. Cl.[6] ........ A61K 35/78; A61K 7/48

[52] U.S. Cl. ........ 424/195.1; 424/401; 514/873

[58] Field of Search ........ 424/195.1, 196.1, 424/401; 514/873

[56] References Cited

U.S. PATENT DOCUMENTS

| | | | |
|---|---|---|---|
| 3,620,919 | 11/1971 | Hardman | 435/267 |
| 4,481,185 | 11/1984 | Grollier et al. | 424/59 |
| 4,551,330 | 11/1985 | Wagman et al. | 424/59 |
| 4,804,531 | 2/1989 | Grollier et al. | 424/47 |
| 5,165,915 | 11/1992 | Tokubo et al. | 424/63 |

FOREIGN PATENT DOCUMENTS 2 050 825 1/1981 United Kingdom .

*Primary Examiner*—David M. Naff
*Assistant Examiner*—Janet M. Kerr
*Attorney, Agent, or Firm*—Young & Thompson

[57] ABSTRACT

The invention relates to an oil-in-water type emulsion for moisturizing the upper layers of the epidermis, comprising a lipid phase dispersed in an aqueous phase. The lipid phase is composed of apolar plant products comprising from 5 to 15% by weight of plant oils and from 6 to 15% by weight of plant waxes. The aqueous phase comprises from 0.5 to 4% by weight of plant gums and from 2 to 7% by weight of polysaccharide-rich plant extracts. The percentages are expressed relative to the total weight of the emulsion. The composition of the preferred oil-in-water emulsion consists of 1 to 3% phosphatidylcholine, 0.5 to 2% guar gum, 0.5 to 2% carob gum, 0.5 to 2% aloe vera powder, 2 to 5% yucca powder, 15 to 40% glycerol, 5 to 10% balanites oil, 5 to 10% jojoba oil, 1 to 5% carnauba wax, and the balance essentially water.

1 Claim, 3 Drawing Sheets

TIME (H)
0.5
1
2
4
6
7
INCREASE IN DEGREE OF MOISTURIZATION
0
10
20
30
40
50

MIXTURE COMPRISING PLANT EXTRACTS FOR MOISTURIZING THE UPPER LAYERS OF THE EPIDERMIS

BACKGROUND OF THE INVENTION

The present invention relates to a mixture comprising plant extracts for moisturizing the upper layers of the epidermis.

Water forms part of the constitution of the skin. This water is distributed heterogeneously. There also exists a decreasing gradient from the dermis (which contains 70% water) to the outside, the epidermis containing only 12 to 15% water.

The water in the epidermis is essentially intracellular. A skin whose stratum corneum (SC) is well moisturized has a pleasant appearance. It is the water which gives the skin its mechanical properties and its permeability, inter alia. The stratum corneum should not stray from an equilibrium value, otherwise it is liable to suffer an adverse change in its mechanical and physiological properties. It is thus obligatory to keep the skin moisturized.

Starting with the study of the rôle of various plant compounds, in particular of plants from arid regions, in the uptake of water and in its retention in the plant tissues, the authors of the present invention addressed themselves to means of using the moisturizing properties of these compounds to maintain good moisturization of the skin.

These authors more particularly addressed two types of compounds with complementary and synergistic activity, that is to say combining a moisturizing and anti-dehydrating power, in order to obtain long-lasting improvement in the moisturization of the upper layers of the epidermis.

SUMMARY OF THE INVENTION

The authors of the present invention thus obtained a mixture from polar plant compounds (plant gums, polysaccharides) and from apolar plant compounds (plant waxes and oils) which can be incorporated as a moisturizing active principle into cosmetic or pharmaceutical compositions for moisturizing the upper layers of the epidermis.

Thus the present invention relates to an emulsion of oil-in-water type for moisturizing the upper layers of the epidermis, comprising a lipid phase dispersed in an aqueous phase,

- the lipid phase being composed of apolar plant products comprising:
  - from 5 to 15% by weight of plant oils;
  - from 6 to 15% by weight of plant waxes;

and

- the aqueous phase comprising:
  - from 0.5 to 4% by weight of plant gums;
  - from 2 to 7% by weight of polysaccharide-rich plant extracts;

the percentages being expressed relative to the total weight of the emulsion.

The invention is also directed towards cosmetic or pharmaceutical compositions for moisturizing the upper layers of the epidermis, comprising this emulsion as moisturizing active principle.

The invention is moreover directed towards the use of the said emulsion for the manufacture of cosmetic or pharmaceutical compositions for moisturizing the upper layers of the epidermis, as well as the use of the emulsion for improving the moisturization of the upper layers of the epidermis in cosmetology.

Lastly, the invention relates to a method for improving the moisturization of the upper layers of the epidermis by applying a cosmetic composition comprising the abovementioned emulsion as active principle.

BRIEF DESCRIPTION OF THE DRAWINGS

The results of the corneometry and thermal conductivity measurements are represented in the figures below, in which.

DETAILED DESCRIPTION OF THE INVENTION

Figure 1:
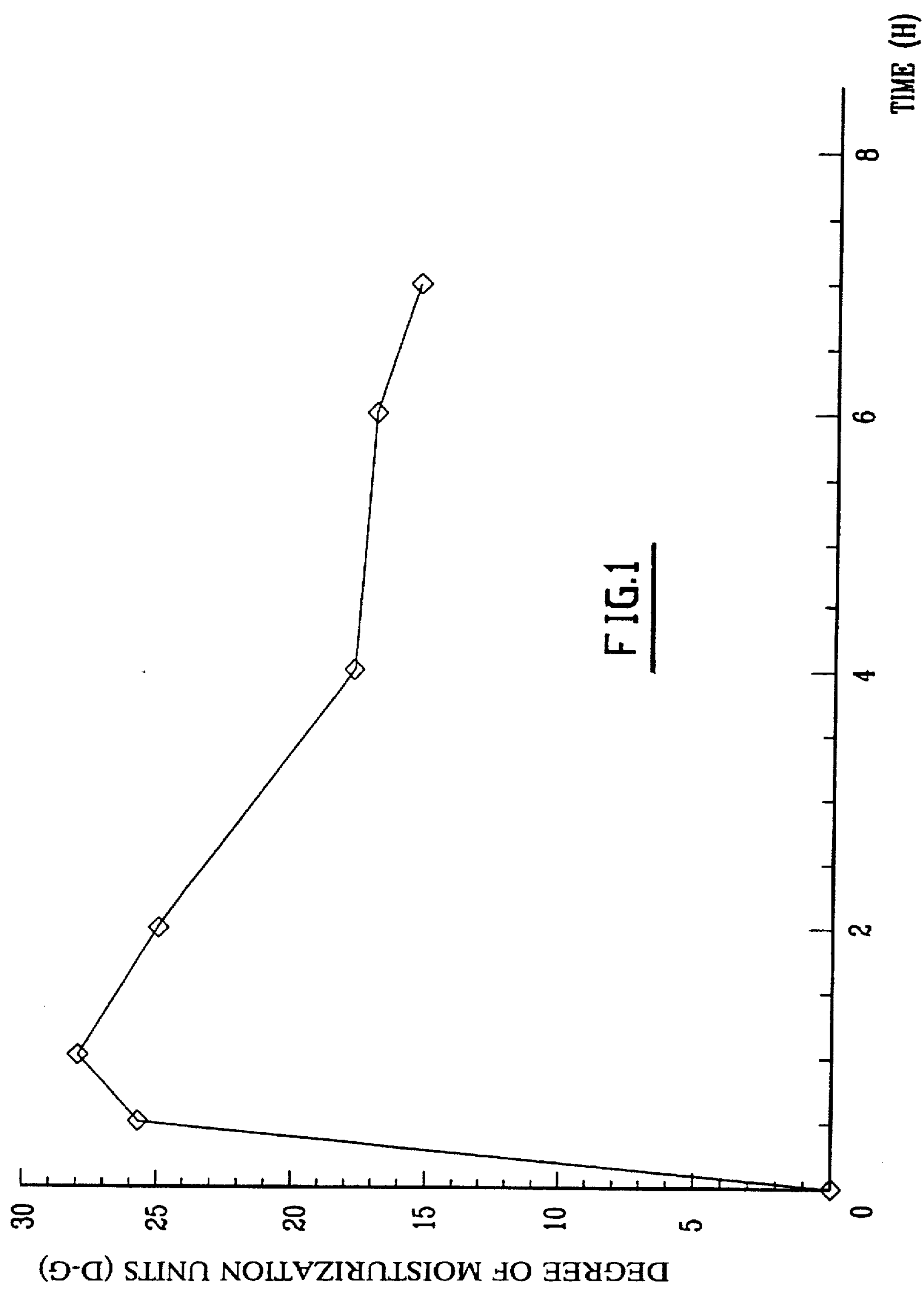
FIG. 1 represents the measurement by corneometry of the degree of moisturization of the mixture I applied to a forearm for 7 hours (arbitrary units)
Figure 2:
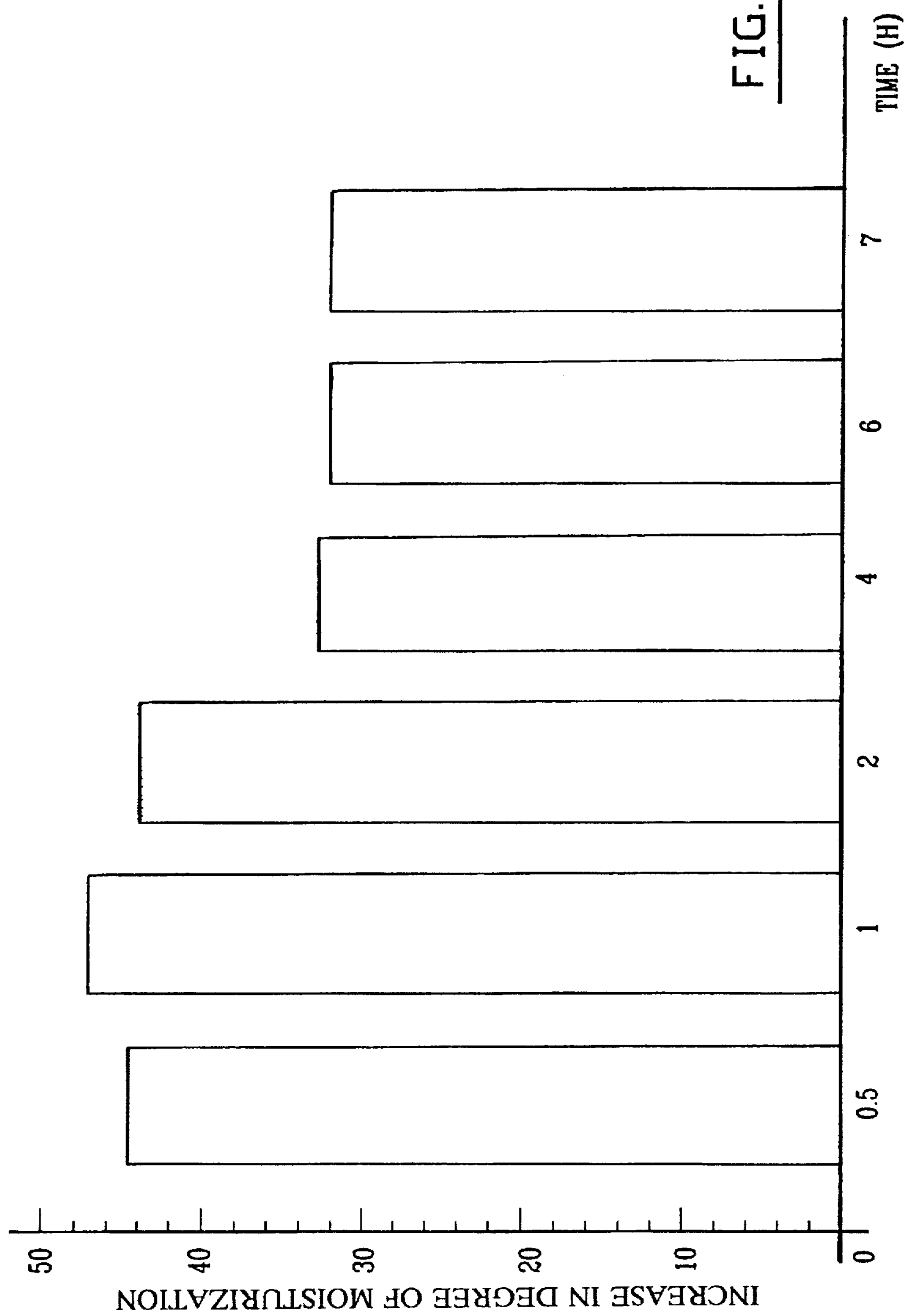
FIG. 2 represents the increase in the degree of moisturization on the same mixture expressed as a %.
Figure 3:
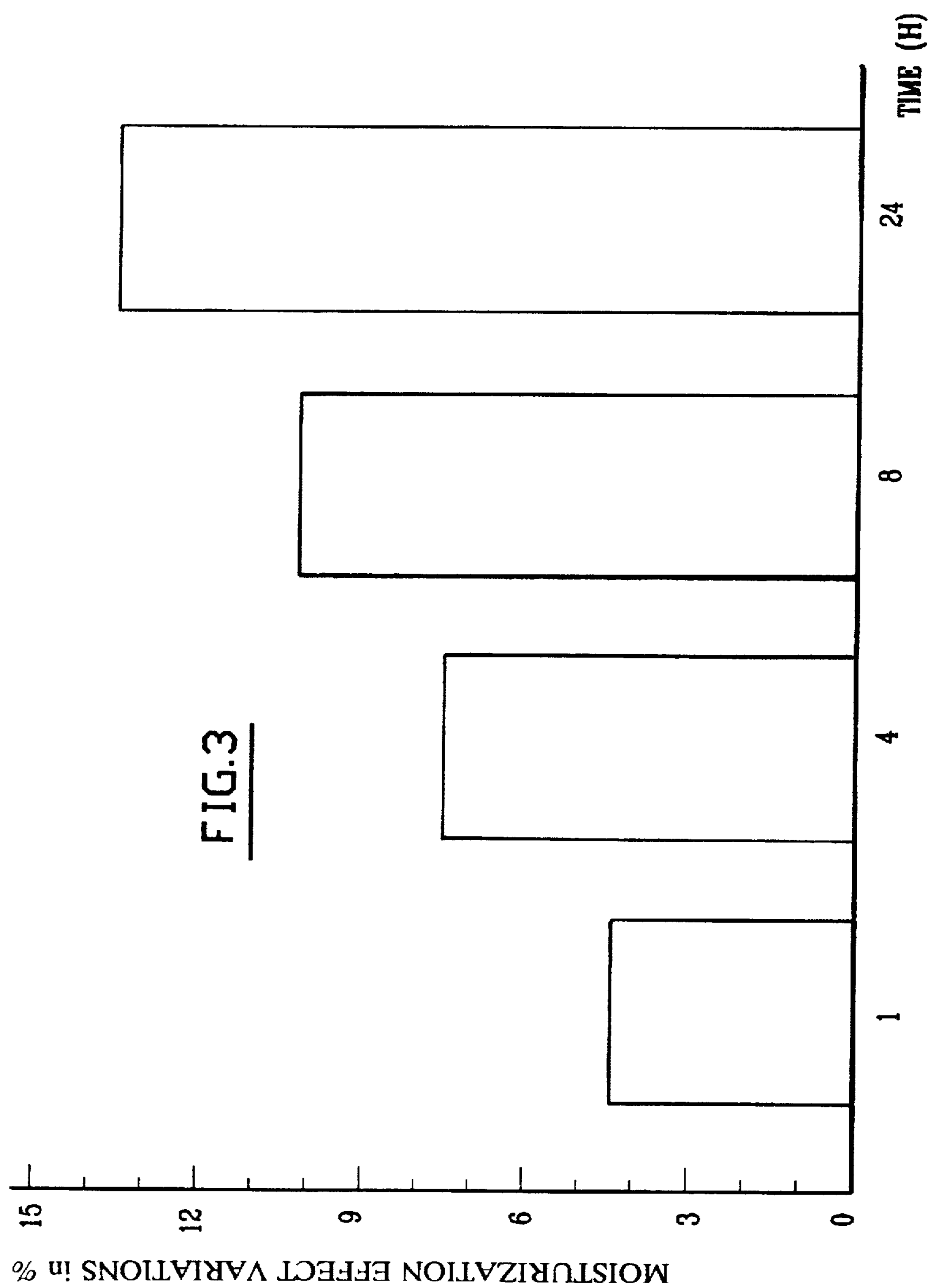
FIG. 3 represents the measurement of the moisturizing effect of a cosmetic composition comprising 2% of the mixture I according to the invention (by conductimetry, in 12 out of 24 cases).

The emulsion according to the invention comprises constituents which are advantageously selected as a function of their moisturizing properties. In particular, it comprises:

- plant gums and polysaccharide-rich plant extracts, selected from one or more of the following compounds: guar gum, carob gum, gum arabic, gum tragacanth, sterculia gum, extract of yucca, extract of aloe vera and extract of opuntia;
- plant oils, which are preferably plant oils rich in polyunsaturated fatty acids (PUFA) selected from one or more of the following compounds: balanites oil, sesame oil and baobab seed oil;
- plant waxes selected from carnauba wax, jojoba oil (liquid wax) and candelilla wax.

The plant extracts used in the emulsion according to the invention advantageously come from plants capable of growing in arid or semi-arid regions.

The plant polysaccharides of the emulsion are mucilages which possess the characteristic of taking up and strongly retaining water by means of their hydrophilic macromolecular properties.

The plant oils limit the evaporation of water and act at two levels: on the one hand, by virtue of their hydrophobic properties, on the other hand, by virtue of the incorporation of fatty acids, in particular unsaturated fatty acids, into the stratum corneum, these fatty acids reinforcing the efficiency of the skin barrier.

Lastly, the waxes, which are naturally present at the surface of leaves, make it possible to limit the water losses from the plants by virtue of their hydrophobic nature. When incorporated into the emulsion according to the invention, these plant waxes make it possible to limit water losses from the skin by virtue of a film-forming effect and an effect of reducing the transepithelium water loss (TEWL).

According to a preferred variant, the emulsion of the invention also comprises 10 to 50% by weight of a polyol with a high wetting power, selected from, for example, glycerol, sorbitol, sucrose and lactose.

Advantageously, the emulsion also comprises amphiphilic molecules such as, in particular, phospholipids, which are a natural constituent of cell membranes. These phospholipids are selected in particular from lecithins (which may contain varying percentages of phosphatidylcholine, phosphatidylethanolamine or phosphatidylinositol) and are preferably present in a proportion of from 1 to 5% by weight in the mixture.

A preferred mixture in emulsion form according to the invention is composed of:

| | | | |
|---|---|---|---|
| Phosphatidylcholine | 1 to 3% | and preferably | 2% by weight |
| Guar gum | 0.5 to 2% | | 0.7% by weight |
| Carob gum | 0.5 to 2% | | 0.7% by weight |
| Aloe vera powder | 0.5 to 2% | | 1% by weight |
| Yucca powder | 2 to 5% | | 2.5% by weight |
| Glycerol | 15 to 40% | | 40% by weight |
| Balanites oil | 5 to 10% | | 10% by weight |
| Jojoba oil | 5 to 10% | | 10% by weight |
| Carnauba wax | 1 to 5% | | 3% by weight |
| Water | qs | | qs |

The degree of incorporation of an emulsion according to the invention into cosmetic or pharmaceutical compositions may range from 1.0 to 10% depending on the desired level of moisturization.

The presentation in emulsion form allows its constituents to be absorbed more easily by the skin, on account of the lowering of the surface tension of the fatty substances, thereby promoting much more intimate contact with the constituent elements of the epidermis.

Moreover, this presentation makes it possible to intimately mix elements of incompatible physical nature but of complementary properties. This therefore allows the cumulation and synergism of activity of products which are naturally immiscible.

The emulsion according to the invention moreover has the advantage of containing only natural products and additives (free of chemical modification) or compounds of natural origin (natural compounds which have undergone chemical modifications).

This emulsion described above may be obtained according to the following procedure:

The plant extracts and plant gums are dry extracts in powder form, obtained by chemical extraction or from concentrated and dried saps. These plant extracts and other compounds and additives used are available from suppliers. The physicochemical characteristics of these compounds are described in the literature or are advised by the suppliers.

For example, a powdered extract of aloe vera may be obtained by grinding and trituration of aloe vera leaves to give a liquid gel of aloe vera, and then by lyophilization of this gel.

It is also possible to use a product based on powdered yucca containing 50% of extract of yucca, available from Garuda International. This product is prepared by extraction of yucca stems with water, addition of maltodextrin to obtain a suspension whose dry extract consists of 50% by weight of maltodextrin and 50% of material extracted from yucca, and drying by spraying of this suspension to give a final powdered product.

The preparation of the mixture consists in:

incorporating in a mixer demineralized water which is heated to between 75° and 80° C.;

dissolving the phospholipid fraction (lecithin) in the aqueous phase, with vigorous stirring and heating so that it is dispersed (the mixture then becomes milky and opalescent);

predispersing, in a separate container, the plant extracts and gums in glycerol and checking the homogeneity of this premix;

introducing this premix into the aqueous phase with vigorous stirring and then leaving the plant gums to swell for 30 minutes at a temperature of between 70° and 80° C.;

in parallel, heating the waxes and the oils to 80° C. and checking that the various constituents have melted properly;

after having checked the homogeneity of the two phases, introducing the fatty phase into the aqueous phase and then stirring for 5 to 10 minutes at high speed;

cooling with stirring to bring the mixture to 25° C.

A mixture of oil-in-water emulsion type is thus obtained, which will be used subsequently for the manufacture of cosmetic or pharmaceutical compositions for moisturizing the upper layers of the epidermis.

The moisturizing properties of the emulsion (mixture I) comprising the following compounds will be described below, by way of illustration:

| | | |
|---|---|---|
| Phosphatidylcholine | 2% | by weight |
| Guar gum | 0.7% | " |
| Carob gum | 0.7% | " |
| Aloe vera powder | 1% | " |
| Yucca powder | 2.5% | " |
| Glycerol | 40% | " |
| Balanites oil | 10% | " |
| Jojoba oil | 10% | " |
| Carnauba wax | 3% | " |
| Water | qs | " |

The moisturizing activity of the emulsion is measured by corneometry on the forearm. Its efficacy, when the latter is incorporated in a proportion of 2% into a cosmetic composition, is then measured by thermal conductivity.

The method by corneometry consists in measuring the dielectric properties of the skin before and after application of the product to a defined surface.

The results, expressed in arbitrary units, are converted into a percentage increase.

The method by thermal conductivity makes it possible to measure thermal variations in the skin, which are associated with the variations in the water content of the skin. The results are expressed as cal /cm×°C.×S and may be expressed as a % increase.

The measurements by corneometry show that the mixture of the invention makes it possible to increase the degree of moisturization of the skin by more than 40%, two hours after it is applied.

The moisturization is then maintained at a level of about 30% for up to 7 hours after it is applied. Moreover, the measurements by thermal conductivity make it possible to verify that the moisturizing activity of the mixture incorporated into a cosmetic composition is displayed for up to 24hours, where a percentage increase of about 13% may be observed.

The following examples of compositions in various forms illustrate the present invention.

The moisturizing mixture used in these composition examples is the mixture I defined above.

EXAMPLES

EXAMPLE 1

Composition in cream form

| Phase A | | |
|---|---|---|
| Demineralized water | qs 100% | by weight |
| Preserving agents | qs | " |
| Moisturizing mixture (mixture I) | 4.00% | " |
| Allantoin | 0.10% | " |
| Tetrasodium EDTA | 0.05% | " |
| Carbomer | 0.20% | " |

-continued

| Phase B | | |
|---|---|---|
| CB/C10 triglycerides | 3.00% | " |
| α-bisabolol | 0.20% | " |
| Plant oil | 7.00% | " |
| Cyclomethicone | 4.00% | " |
| Methoxy PEG 17/dodecyl glycol Copolymer | 2.00% | " |
| Karite butter | 5.00% | " |
| Phase C | | |
| L-lysine | qs pH 5.8–6.3 | |
| Fragrance | qs | |

EXAMPLE 2

Composition in milk form

| Phase A | | |
|---|---|---|
| Demineralized water | qs 100% | by weight |
| Preserving agents | qs | " |
| Moisturizing mixture (mixture I) | 3.00% | " |
| Tetrasodium EDTA | 0.05% | " |
| Carbomer | 0.10% | " |
| Phase B | | |
| Ethylhexyl cocoate | 7.00% | " |
| Isopropyl adipate | 5.00% | " |
| Cetyl palmitate | 1.00% | " |
| Plant oil | 3.00% | " |
| Dimethicone | 2.00% | " |
| Ethoxylated fatty alcohol | 3.00% | " |
| Phase C | | |
| NaOH | qs pH 6.00 | |
| Fragrance | qs | |

EXAMPLE 3

Composition in lotion form

| Phase A | | |
|---|---|---|
| Demineralized water | qs 100% | by weight |
| Tetrasodium EDTA | 0.05% | " |
| PEG 400 | 2.00% | " |
| Preserving agents | qs | |
| 96° alcohol | 5.00% | " |
| Oleyl alcohol 20 EO | 0.50% | " |
| Fragrance | qs | |
| Moisturizing mixture (mixture I) | 1.50% | " |
| Dye | qs | |

EXAMPLE 4

Composition in gel form

| Phase A | | |
|---|---|---|
| Demineralized water | qs 100% | by weight |
| Preserving agents | qs | " |
| Carbomer | 0.60% | " |
| Xanthan gum | 0.10% | " |
| Moisturizing mixture (mixture I) | 2.00% | " |
| Phase B | | |
| 96° ethanol | 10.00% | |
| Dimethicone copolyol | 3.00% | |
| Fragrance | qs | |
| Phase C | | |
| NaOH | qs pH 6.00 | |
| Dyes | | |

We claim:

1. An emulsion for moisturizing the upper layers of the epidermis comprising the following compounds by weight:

| | |
|---|---|
| Phosphatidylcholine | 1–3% |
| Guar gum | 0.5–2% |
| Carob gum | 0.5–2% |
| Aloe vera powder | 0.5–2% |
| Yucca powder | 2–5% |
| Glycerol | 15 to 40% |
| Balanites oil | 5 to 10% |
| Jojoba oil | 5 to 10% |
| Carnauba wax | 1 to 5% |
| And water to 100%. | |

* * * * *